United States Patent [19]
Brown et al.

[11] Patent Number: 6,159,699
[45] Date of Patent: Dec. 12, 2000

[54] ENZYME LINKED CHEMILUMINESCENT ASSAY

[75] Inventors: Richard Charles Brown; Ian Weeks, both of Cardiff, United Kingdom

[73] Assignee: Molecular Light Technology Limited, Cardiff, United Kingdom

[21] Appl. No.: 08/979,827

[22] Filed: Nov. 24, 1997

Related U.S. Application Data

[63] Continuation of application No. 08/438,723, May 10, 1995, abandoned.

[30] Foreign Application Priority Data

May 10, 1994 [GB] United Kingdom .................. 9409223

[51] Int. Cl.$^7$ .......................... G01N 33/53; G01N 33/566
[52] U.S. Cl. .............. 435/7.1; 435/7.5; 435/7.9; 435/7.91; 435/7.92; 435/6; 435/975; 435/966; 435/968; 436/501
[58] Field of Search .................. 435/7.5, 7.9, 7.91, 435/7.92, 968, 975, 6, 966; 436/501

[56] References Cited

FOREIGN PATENT DOCUMENTS

| 0256932 | 5/1987 | European Pat. Off. . |
| 609885 | 3/1994 | European Pat. Off. . |
| 94/04538 | 8/1993 | WIPO . |
| 94/11734 | 11/1993 | WIPO . |

*Primary Examiner*—Christopher L. Chin
*Assistant Examiner*—Pensee T. Do
*Attorney, Agent, or Firm*—Jones, Tullar & Cooper, PC

[57] ABSTRACT

A method is provided for determining in a medium the presence or amount of an analyte which is capable of binding to a ligand partner to form a ligand complex, which method comprises: (a) contacting the medium with either: (i) a ligand partner conjugated with an enzyme being capable of catalysing a reaction, or one or more reactions in a cascade thereof, to produce hydrogen peroxide, or (ii) a ligand partner and either a competing analyte or an analog of said analyte, a competing analyte or analyte analog being capable of forming a ligand complex with the ligand partner and the competing analyte or analyte analog being conjugated with an enzyme capable of catalysing a reaction, or one or more reactions in a cascade thereof, to produce hydrogen peroxide, (b) optionally separating complexed and uncomplexed enzyme conjugates, (c) causing or allowing the reaction or cascade of reactions to occur to produce hydrogen peroxide by contacting the complexed or uncomplexed enzyme conjugate with a corresponding enzyme substrate; (d) contacting hydrogen peroxide with a substance capable of exhibiting chemiluminescence in the presence of hydrogen peroxide selected from the group consisting of acridinium compounds and analogs thereof having a conjugate base with a pKa less then 9 to generate a chemiluminescent reaction, and (e) detecting the occurrence of said chemiluminescent reaction to determine the presence or amount of the analyte. Kits for use in connection with the method are also disclosed.

28 Claims, 1 Drawing Sheet

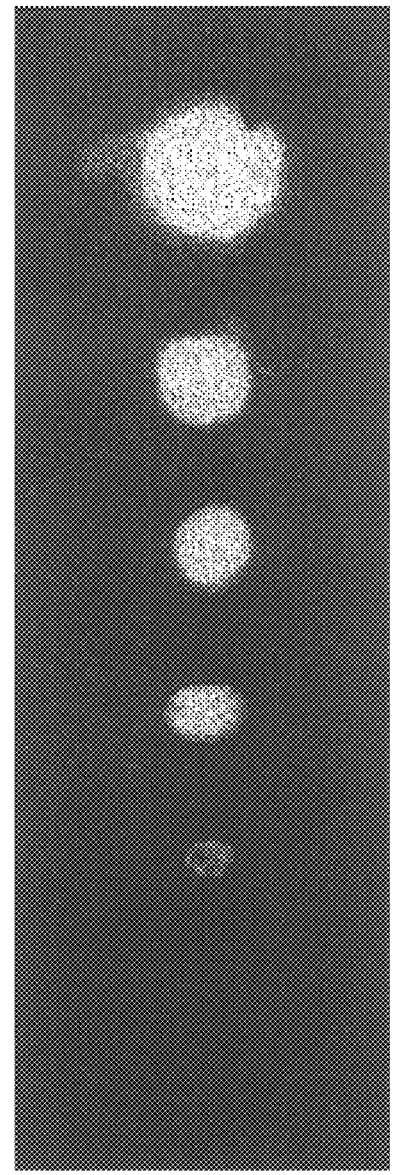

ENZYME LINKED CHEMILUMINESCENT ASSAY

This is a continuation of application Ser. No. 08/438,723 filed on May 10, 1995, now abandoned.

BACKGROUND TO THE INVENTION

This invention relates to an assay or detection method which employs an enzyme linked chemiluminescent endpoint signalling system for the detection and measurement of compounds of interest in assay systems employing ligand binding techniques.

Such ligand binding techniques depend upon the facility inherent in biological molecules such as receptors, antibodies and nucleic acids to bind with a high degree of specificity their respective analogous partner ligand. Owing to this specificity, such techniques have found widespread application in the detection and measurement of many entities ranging from simple chemicals to complex biological molecules, including peptides, proteins, carbohydrates and nucleic acids. Consequently the technique of ligand binding has become one of the most important tools for investigation and assay, and has thus found universal application.

In such ligand binding systems, the specific binding reaction occurs when the ligand is presented to the ligand partner compound. Examples include the antibody-antigen reaction, and the hybridisation of complementary nucleic acid sequences. A key feature inherent to all ligand binding assay systems is that, in order to monitor the progress of such binding and thus to obtain a qualitative and/or quantitative indication of the degree of such binding, it is necessary to label, either directly or indirectly, at least one of the ligand partners participating in the ligand binding reaction. This labelled ligand can then be employed to generate a measurable signal by which the reaction is monitored. The relative quantity of signal generated by the labelled ligand will be proportional to the quantity of labelled ligand present and thus can serve to indicate the concentration of the labelled ligand. Examples of such signal generators include radioactive nuclides ($^{125}$I, $^{3}$H, $^{14}$C, $^{32}$P), chemiluminescent or fluorescent compounds (acridinium esters, lanthanide chelates) and enzymes (peroxidase, phosphatase).

Such labels are synthesised by chemically coupling the signal generator 'label' to the ligand so that they do not perturb its binding characteristics but enable its presence to be measured by the appropriate detection technology. The choice of signal generating labels is influenced by factors such as ease and sensitivity of detection, and the ability to incorporate readily such compounds chemically into the particular ligand. Classically the first class of compounds to be so employed were radionuclides. These can be incorporated into biological molecules and render themselves detectable by virtue of their radioactive emissions which can be monitored by appropriate technology such as scintillation counting and high energy photon sensitive chemical films. However, radioactive moieties suffer from problems associated with their radioactive decay such as safety and instability, as well as limited sensitivity of detection with certain nuclides. Consequently alternative non-isotopic signal generating systems have been sought. These non-isotopic labels are chemically linked to one of the components participating in the ligand binding reaction.

Examples of such alternative non-isotopic signal generating systems include fluorescence, where the output signal is generated by the excitation of a suitable molecular adduct, chemiluminescence where the output signal is generated by chemical modification of the signal compound, or enzymes where there occurs an enzyme dependent secondary generation of signal such as the formation of a coloured product from a non-coloured substrate.

British Patent Specification 2 112 779 describes techniques where acridinium salts have been successfully employed as direct signal generating labels in ligand binding assays. Here the acridinium salt is covalently coupled directly to the ligand. Following the assay procedure the luminescence is measured by subjecting the acridinium salt, linked to the ligand specifically captured in the ligand binding complex, to exposure to peroxide in strong alkali (pH 14). Under these conditions an acridinium ester bond, for example, is broken leading to the formation of an excited product molecule which relaxes to its ground state with loss of energy in the form of photons. These photons can then be quantified by standard luminometric techniques. Typically, though not exclusively, the release of photons is rapid with the signal generating reaction being completed within 1–2 seconds when excess quantities of initiating alkaline peroxide are present. In order for this reaction to be monitored, the addition of one or more initiator compounds must necessarily take place when the reactants are in physical proximity to the luminometric device. This can present limitations to its application, particularly when detecting the signal from labelled ligand captured on a flat surface such as a gel, membrane or tissues. In consequence, despite its very high sensitivity, the employment of acridinium salt luminescence has until now been restricted to ligand binding systems where reactants are enclosed in tubes which can be placed in luminometers prior to in situ addition of initiator reagents.

In the case of enzymes as primary signal generators, the action of the enzyme on an appropriate substrate may itself lead to the generation of a secondary signal which is, for example, chemiluminescent or fluorescent in nature. In this situation the role of the labelling enzyme is either direct, that is to convert the substrate itself from an inactive to an active and therefore detectable form, or indirect, that is to convert the substrate from an inactive to active substance which is itself an initiator or co-factor in the conversion of an inactive to active compound. An example of the former is the direct action of alkaline phosphatase on stable dioxetanes, where removal of a phosphate group renders the dioxetanes unstable with a consequent release of quantifiable luminescence. An example of the latter is the indirect action of peroxidase on luminol where luminescence is generated from enzyme catalysed production of active oxygen species by breakdown of peroxide substrate. In both these examples, after a suitable incubation period, luminescence is relatively long lived as it depends upon the generation of product by the signal enzyme, a process which is essentially continuous until the available substrate is consumed. Of those systems which have found the most widespread application, the signal intensity is inherently low thus limiting the scope of application; in order to overcome this problem, such systems require the use of enhancers (for example, para-iodo-phenol) or amplifiers (for example, fluorescent polymers) thereby increasing the complexity of these signal generating methods.

Ligand binding assays employing oxidase enzymes such as glucose oxidase as signal generating labels have been described previously. In these systems the presence of the ligand-linked oxidase enzyme is monitored indirectly by coupling the reaction to peroxidase enzymes such as horseradish peroxidase to generate active oxygen species which combine with a suitable colourless soluble reducing agent to produce a coloured product. This technique however suffers from poor detectability.

Arakawa et al (Clinical Chemistry vol 31, pp 430–434, 1984) describe a ligand binding assay using glucose oxidase coupled bis-oxalate ester generated luminescence employing a fluorescent dye. Alternatively a method has been described by Kiriyama et al (Clinica Chimica Acta vol 220, pp 201–209, 1993) where the peroxide produced from glucose oxidase linked ligand is monitored by its capacity to generate luminol chemiluminescence in the presence of ferricyanide.

However both these methods are insensitive and extensive duration (overnight) of pre-incubation of the enzyme linked ligand with glucose substrate is required to generate sufficiently detectable concentrations of peroxide.

The inventors have developed a method which benefits from the high photon emission of chemiluminescent acridinium compounds and their analogs, without requiring the lengthy pre-incubation periods of typical enzyme linked assays, and whilst providing a sustained photon emission as compared with the more rapid light emission normally associated with chemiluminescent acridinium compounds and their analogues. The sustained emission means that the high sensitivity of chemiluminescent acridinium compounds and their analogues may now be used for gels, membranes and tissues, where many sites may be assayed simultaneously and the photon emission recorded photographically or by other imaging methods. Further, the sustained emission does not require that the reagents are applied to all the gel sites simultaneously. The shortened incubation period means that assays may be carried out in real time, rather than overnight.

The methods may however be used in many applications other than on gels, membranes or tissues.

SUMMARY OF THE INVENTION

Accordingly, in one aspect of this invention, there is provided a method of determining in a medium the presence or amount of an analyte which is capable of combining with a ligand partner to form a ligand complex, which method comprises:

(a) contacting said medium with either:
  (i) said ligand partner conjugated with an enzyme capable of catalysing a reaction, or one or more reactions in a cascade thereof, to produce hydrogen peroxide, or
  (ii) said ligand partner and either competing analyte or an analog of said analyte, said competing analyte or analyte analog being capable of forming a ligand complex with said ligand partner and being conjugated with an enzyme capable of catalysing a reaction, or one or more reactions in a cascade thereof, to produce hydrogen peroxide, (b) optionally separating complexed and uncomplexed enzyme conjugates, (c) causing or allowing said reaction or cascade to occur to produce hydrogen peroxide, (d) reacting said hydrogen peroxide with a chemiluminescent substance selected from the group comprising acridinium compounds and their analogs including phenanthridine, quinoline and benzacridine compounds, to generate a chemiluminescent reaction, and (e) detecting, measuring or observing the photon emission during said chemiluminescent reaction to determine the presence or amount of said analyte.

The method of this invention may be used in many different applications. It may be used for detecting materials on a gel using enzyme-labelled antibodies or enzyme-labelled nucleic acid probes and so on. It may also be used in homogeneous assays, heterogeneous assays, two-site assays and many other assay and labelling techniques well known to those skilled in the art. In heterogeneous assays, it will be necessary to separate the ligand complex bound and unbound fraction. This may be done using any of the techniques available to those skilled in the art, e.g. immobilized or solid phase antibodies or antigens, and so on. Alternatively, the conjugate of this enzyme and ligand partner or analyte or analog analyte (as the case may be) may be designed so that, on binding to form a ligand complex, the enzyme is modified or caused to change from active to inactive or vice versa.

In another aspect, this invention provides a kit for use in the assay or detection in a sample of an analyte which is capable of combining with a ligand partner to form a ligand complex, which kit comprises:

a first reagent containing either:
  (i) said ligand partner conjugated with an enzyme capable of catalysing a reaction or one or more reactions in a cascade thereof to produce hydrogen peroxide, or
  (ii) competing analyte or an analog of said analyte capable of forming a ligand complex with said ligand partner, said competing analyte or analyte analog being conjugated to an enzyme capable of catalysing a reaction, or one or more reactions in a cascade thereof, to produce hydrogen peroxide, and a second reagent containing a chemiluminescent compound selected from the group comprising acridinium compounds and their analogs, including phenanthridine, quinoline and benzacridine compounds, which react with hydrogen peroxide to produce photon emission.

In a further aspect, this invention provides a kit for use in the assay or detection in a sample of an analyte which is capable of combining with a ligand partner to form a ligand complex, in which method said sample is first contacted with either:

(i) a moiety comprising said ligand partner conjugated with an intermediate ligand partner capable of binding with a respective complementary intermediate ligand partner in an intermediate ligand binding complex, or (ii) said ligand partner and a moiety comprising competing analyte or an analog of said analyte, said competing analyte or analyte analog being capable of forming a ligand complex with said ligand partner and being conjugated with an intermediate ligand partner capable of binding with a respective complementary intermediate ligand partner in an intermediate ligand binding complex, said kit comprising a first reagent containing either:
  (i) a moiety comprising said ligand partner conjugated with said intermediate ligand partner, or
  (ii) said ligand partner and a moiety comprising competing analyte or an analog of said analyte, said competing analyte or analyte analog being capable of forming a ligand complex with said ligand partner and being conjugated with said intermediate ligand partner, a second reagent containing a conjugate of said complementary intermediate ligand partner coupled to an enzyme capable of catalysing a reaction or one or more reactions in a cascade thereof, to produce hydrogen peroxide and a third reagent containing a chemiluminescent compound selected from a group comprising acridinium compounds and their chemiluminescent analogs, including phenanthridine, quinoline and benzacridine compounds, which react with hydrogen peroxide to produce photon emission.

According to preferred aspects of this invention, the labelled ligand is directly or indirectly linked to an oxidase enzyme which under the correct conditions is capable of catalysing the generation of initiator peroxide from the respective oxidisable substrate. The addition of substrate and acridinium salt to the bound oxidase enzyme labelled ligand complex leads to a rapid generation of a long-lived chemiluminescent signal which can be monitored after a short (typically 5 minutes) preincubation time. The acridinium salt is presented to the ligand linked oxidase in a solution which also contains the respective substrate. This solution must be buffered at a pH which is within the working range of the oxidase enzyme, which is generally in the range pH 5 to 7. The reactivity of the acridinium ester must be such that it will be capable or reacting within this pH range at a sufficiently high quantum yield. The emission of light can be monitored by conventional detection systems, but is long lived in contrast to ligand binding signal generating systems employing direct labelling with acridinium salts described above.

Preferred embodiments of this invention have two distinct and novel advantages relative to previously described ligand binding systems employing acridinium salts as signal generators, namely (a) the signal is long lived, and (b) the signal generator yields high light intensities in the absence of in situ initiator reagent addition. Further, in contrast to the most widely used enzyme chemiluminescent ligand binding signal generating systems, no amplifier or enhancer "cofactors" are required, although in some instances, these may be used if desired.

DESCRIPTION OF THE PREFERRED EMBODIMENTS

The two main components of this system are the enzyme which is chemically coupled either directly or indirectly to ligand, and the acridinium salt which reacts with generated peroxide to produce the chemiluminescent signal.

The nature of the enzyme used as ligand label can be:

(a) any of those which are classified as oxidases. A suitable enzyme is, for example, glucose oxidase which catalyses the oxidation of glucose; others include xanthine oxidase, uricase, galactose oxidase and others whose catalysis results in the generation of peroxide from the respective substrate;

(b) other enzymes whose action is to generate an oxidase substrate from a precursor molecule in the presence of the respective oxidase in solution; and example of such a ligand label is glucose synthetase.

The labelling enzyme can be linked directly to ligand by chemically coupling using established linking techniques. Alternatively, the enzyme may be indirectly linked to the ligand by an intermediate ligand binding system. One example of such an indirect system involves the utilisation of the established avidin-biotin system, in which these two substances themselves participate in a binding reaction with extremely high affinity. In this example, one component, for example biotin, is chemically linked to ligand (such as an antibody or a nucleic acid sequence, many examples of such biotinylated ligands are available commercially), and the oxidase enzyme to avidin. Following the ligand binding reaction, the ligand complex, containing biotinylated ligand, is exposed to enzyme linked avidin, allowing the capture of enzyme by the ligand complex. The chemiluminescent reaction can then occur by the subsequent exposure of this indirectly enzyme labelled ligand complex to solution containing the acridinium salt and respective enzyme substrate.

The nature of the acridinium salt is selected to be such that it reacts at high efficiency with the generation of high luminescent intensity at the pH range optimal for the activity of the oxidase enzymes employed as ligand label. For example, the optimal pH range for the activity of glucose oxidase is between pH 5.0 and 7.0, therefore it is desirable to employ a species of acridinium salt which can react at this pH in order to monitor the amount of glucose oxidase activity present in a ligand binding reaction.

Acridinium salts useful for this purpose are those which have conjugate bases with pKa values less than 9 or preferably less than 8. Examples of such acridinium salts are phenyl esters where the phenyl moiety possesses electron withdrawing groups such a halogen, carbonyl or nitro situated in positions on the phenyl moiety such that the required pKa is achieved. Electron donating groups may also be present provided that they do not oppose the electron withdrawing groups to the extend of increasing the pKa above the desired range. The design and synthesis of chemical moieties having a given pKa value is well-known to those skilled in the art. The prediction of pKa values for said moieties can be readily made, for example as described by Perrin et al (Perrin D D et al, pKa Prediction for Organic Acids and Bases, Chapman and Hall, London, 1981). Further examples would be amides, aliphatic esters and thioesters containing electron withdrawing groups. In a further aspect, such suitable acridinium salts may also contain hydrophilic groups to improve the solubility of said compounds in aqueous media. The introduction of hydrophilic groups such as sulphonates and hydroxyls is well-known to those skilled in the art.

The selection and design of suitable acridinium compounds is well within the competence of one skilled in the art. British Patent No. 2 112 779 describes the synthesis of one particular compound, and many documents following this pioneering work describe alternative compounds; see for example EP-A 257S41, 273115, 322926 and 324202, which describe chemiluminescent compounds having acridinium moieties which could be used in the present invention although it will of course be appreciated that reactive groups required for the covalent coupling to substances of biological interest in the above work are not needed in the present invention. Furthermore, reference is made to GB-A-1461877 which describes suitable chemiluminescent compounds for use in this invention.

In a further embodiment, it is possible to make use of the ability of the enzyme conjugate to produce an accumulation of hydrogen peroxide or intermediate product prior to the addition of the chemiluminescent acridinium salt. This has the advantage of making full use of the ability of one molecule of enzyme to produce many molecules of product and of making use of a wider range of acridinium salts other than those which undergo chemiluminescent reactions within the optimal pH range of the enzyme. Thus in a particular aspect, glucose would be added to a glucose oxidase signalling conjugate and left to react for a predetermined time interval. A solution of acridinium salt would then be added followed by a solution of sodium hydroxide to facilitate the chemiluminescent reaction. The intensity of emitted light would then be detected and/or quantified during a predetermined time interval. Several variations of this typical scheme can be envisaged by one skilled in the art.

FIELD OF PREFERRED APPLICATIONS

It is envisaged that the technique disclosed herein will have widespread utility within the field of ligand binding assays. There are several distinct categories of ligand binding assay system in which this invention may thus have application, and examples of these are listed below.

(1) Immunoassay where the unique specificity of antibodies for their respective partner antigens is exploited to enable quantification of the antigen or antibody. The rate and degree of reaction of ligand binding is proportional to the amount of antigen and/or antibody present and is monitored by labelling of one of the partner ligands. Immunoassays are well known to those skilled in the art and this technique is exemplified by the work of Tijssen (Tijssen P, Practice and Theory of Enzyme Immunoassays, Laboratory Techniques in Biochemistry and Molecular Biology vol 15, Elsevier Amsterdam 1990).

(2) Nucleic acid analysis in which the unique specificity of nucleotide sequences for their respective complementary nucleotide sequences is exploited to enable identification and analysis of such sequences. This specificity has been utilised in examples such as DNA sequencing, DNA "fingerprinting", the identification of markers of genetically linked diseases, and the diagnostic identification of pathogenic organisms. These techniques have a requirement for the qualitative and sometimes quantitative identification of nucleotide sequence binding. Currently a large proportion of the qualitative analysis of nucleotide binding is carried out using gels, and the application of luminescent endpoints employing acridinium salts to this situation has not yet been possible owing to the rapidity of the luminescence signal release. It is therefore envisaged that the technique described herein will have particular application in this area, since current technologies mainly rely on nucleotide sequences labelled with radioactive moieties, with the associated problems of safety and instability.

A particular application of this technique will exploit the ready availability of biotinylated nucleotides, where oxidase enzyme linked streptavidin would be of generic utility in such circumstances. Molecular biology techniques, in particular the analysis of nucleic acids by ligand binding, are well known to those skilled in the art and are exemplified by the work of Brown (Brown T A, Essential Molecular Biology A Practical Approach, Oxford University Press, Oxford, 1991)

(3) Protein analysis on gels where proteins are sorted on the basis of physicochemical characteristics such as size or charge and their qualitative identification is then achieved by probing with specific anti-protein antibodies (Western Blotting). Currently identification of ligand binding is commonly achieved by using coloured visual endpoints with consequent limitations in sensitivity of detection. Such techniques are well known to those skilled in the art and are exemplified by the work of Walker (Walker J M, Ed, New Protein Techniques: Methods in Molecular Biology, vol 3, Humana Press, Clifton N.J., 1988).

BRIEF DESCRIPTION OF THE DRAWING

The drawing is a developed sample image obtained in Example 4.

The following examples illustrate the invention and are not intended to limit the scope of the invention in any way.

EXAMPLES

Example 1

An example of the use of this invention is a ligand binding assay for circulating human anti (HIV 1 and 2) antibodies in test samples. Test samples are those in which it has been deemed necessary to determine whether the respective test sample donor is a carrier of one of these pathogenic viruses, for example in blood product screening or sexually transmitted disease clinics. Individuals who have been infected by these viruses will have specific anti-(HIV) antibodies in their circulation.

White plastic 96 well microtitre plates are coated with synthetic peptide sequences corresponding to reactive and conserved regions of the envelope glycoproteins of HIV 1 and HIV 2 retroviruses. This coating is achieved by dissolving the synthetic peptides in a suitable buffered solution such as 0.1M sodium carbonate/bicarbonate pH 9.6 (for the purpose of this and subsequent examples subsequently referred to as "coating buffer") and leaving this solution in contact with the well walls for a period of 18 hours at +4° C. Excess uncoated peptide is then washed away, and unoccupied binding sites on the plastic blocked by the addition of a solution containing 0.05% TWEEN 20 in coating buffer (for the purpose of this and subsequent examples subsequently referred to as "blocking buffer") for 1 hr at room temperature. Wells with the coated peptide are allowed to contact test sample diluted in a suitable vehicle (for the purpose of this and subsequent examples subsequently referred to as "assay diluent"). The assay diluent is a phosphate buffered saline solution containing carrier proteins and detergent. Following a suitable duration of incubation (for example 1 hour at 37° C.) the diluted test sample is removed an the wells washed. If the test sample contained anti-(HIV) antibodies; then a portion of these will have bound to the immobilised HIV antigen on the well wall.

The presence of such bound antibodies can be detected by the addition of glucose oxidase coupled goat anti-(human immunoglobulin). This antibody-enzyme conjugate can be readily synthesised by one skilled in the art using conventional protein conjugation methodology. The conjugate is presented in a solution of assay diluent and is allowed to contact the wells for a further period (for example 30 minutes at 37° C.) to permit binding of the anti-(human immunoglobulin) enzyme conjugate to immunoglobulin, if present from the original test sample.

Following washing away of unbound anti-(human immunoglobulin) enzyme conjugate the presence of bound conjugate and hence anti HIV immunoglobulin in the test sample is determined by the addition of a solution in a suitable buffer, in this example phosphate buffered saline pH 6.5, of the specific enzyme substrate glucose (0.1% w/v) and acridinium ester salt (at a concentration of 1 microgram/ml). The presence of bound glucose oxidase will cause the breakdown of glucose to the product hydrogen peroxide. This in turn activates acridinium ester chemiluminescence. The amount of luminescence will be in direct proportion to the amount of glucose oxidase present in the well.

The luminescence can then be monitored for a period of greater than one hour following addition of the substrate/acridinium ester solution. However, such is the degree of photon output that sufficient measurement can be achieved within a one second measuring time per well. For practical purposes it is convenient to incubate for at least 5 minutes before commencing luminometry.

Sample data from this example are given below:

| DILUTIONS | HIV 1 + VE | HIV 2 + VE | 8 – VE SAMPLES @ 1:20 DILUTION |
|---|---|---|---|
| 1:20 | 981420 | 843210 | 28010 |
| 1:40 | 1010950 | 815700 | 23050 |
| 1:80 | 1021560 | 738310 | 23700 |
| 1:160 | 1033390 | 611470 | 33930 |
| 1:320 | 964720 | 439630 | 52180 |
| 1:640 | 895420 | 279890 | 24400 |
| 1:1280 | 715970 | 168890 | 29010 |
| blank | 8850 | 9020 | 33090 |

The data are given as relative light units per second. The results indicate that the luminescence output, measured as relative light units per second, correlated with the degree of dilution of the positive human sera samples. This indicates that the binding of the glucose oxidase-goat anti-(human immunoglobulin) antibody conjugate can be easily and rapidly monitored following addition of the substrate solution.

EXAMPLE 2

A second example demonstrates the use of the invention employed to indirectly label a ligand. The signal generation is dependent on the indirect binding of a streptavidin-glucose oxidase conjugate to a anti-(human immunoglobulin)-biotin conjugate. Streptavidin specifically binds to its respective partner ligand biotin with very high affinity. Biotinylated ligands are readily available commercially, or can be synthesised by one skilled in the art. The use of biotin-streptavidin as a means of indirect labelling of ligands has widespread application within the field of ligand binding assays.

Opaque, white microtitre plates are coated with human gamma-globulin by incubating the wells in a solution of 50 µg/ml gamma-globulin in coating buffer for 18 hrs at room temperature. Following blocking and washing, the wells are presented with a solution, in assay diluent, containing dilutions of biotinyl-goat anti-(human immunoglobulin). Following incubation for 1 hour at 37° C., the wells are washed and presented with a solution, in assay diluent, containing streptavidin-glucose oxidase conjugate. Following further incubation for 30 minutes at 37° C., the wells are again washed and a solution containing glucose as enzyme substrate (0.1% w/v) and acridinium salt (1 µg/ml) in a phosphate buffered saline pH 6.5 is added to the wells. The chemiluminescence is then quantified as in example 1.

Sample data are given below:

| DILUTION OF BIOTINYL ANTI-HUMAN IMMUNOGLOBULIN | RLU/SECOND |
|---|---|
| ZERO | 9380 |
| 1/8000 | 65170 |
| 1/4000 | 111160 |
| 1/2000 | 170310 |
| 1/1000 | 233590 |
| 1/500 | 305500 |

The data indicate that the luminescence is directly proportional to the concentration of biotinyl anti-(human immunoglobulin) conjugate presented to the wells which in turn is related to the amount of the complex: [human gamma-globulin/biotinyl anti-(human immunoglobulin)/streptavidin glucose oxidase] captured by the wells.

EXAMPLE 3

Example 3 demonstrates how the invention can be applied to act as a signal generating end-point in a "two-site" or "sandwich" immunoassay system. Such two-site immunoassays have found widespread application to the assay of biological samples. They depend upon the employment of one, or, more usually, two antibodies which are capable of specifically reacting with the analyte. Usually one of these is either directly or indirectly linked to a solid support such as para-magnetic particles or the walls of a microtitre plate well and is termed the "capture" antibody. The second antibody is labelled either directly or indirectly with a means of producing an endpoint signal. In the presence of analyte a complex consisting of [capture antibody/analyte/labelled antibody] is generated. In this situation the amount of analyte present is directly proportional to the quantity of the signal at the assay end point.

Thus, this Example describes a two-site immunoassay for human intact parathyroid hormone (PTH) in serum employing a glucose oxidase generated chemiluminescent endpoint. Microtitre plate wells are contacted with a solution of affinity purified sheep anti-(C terminal PTH) at a concentration of 20 µg/ml in coating buffer for 18 hours at room temperature. Following blocking and washing, the wells are presented with varying concentrations of synthetic PTH in serum 100 µl) plus assay diluent (100 µl) containing affinity purified sheep anti-(Nterminal PTH)-glucose oxidase conjugate and incubated for 4 hours at 37° C. with agitation. After a further wash step, bound glucose oxidase activity is measured by adding a solution of acridinium salt in PBS containing glucose, and the subsequent chemiluminescence monitored, as described in Example 1. Sample data are presented in the table:

| PTH CONCENTRATION PG/ML | RLU/SEC |
|---|---|
| 10000 | 97500 |
| 5000 | 61165 |
| 2500 | 34845 |
| 1250 | 21930 |
| 625 | 17495 |
| 312 | 11070 |
| 156 | 8785 |
| ZERO | 5220 |

EXAMPLE 4

This Example describes the application of the invention to the employment of acridinium ester luminescence to monitor ligand binding reactions in a nitrocellulose blot. The technique of separating protein and nucleic acid mixtures into their components by means of differential migration within the matrix of a gel, according to their respective physico-chemical characteristics such as size or charge, has found widespread application within biological science. It is common practice to then immobilise the separated components by a process of blotting onto a nitrocellulose matrix. This permits analysis and identification of the separated components by various techniques, of which one of the most commonly used involves a ligand binding reaction.

For the purposes of demonstrating the application of the invention to the identification of biological compounds immobilised on nitrocellulose by ligand binding, this Example uses a model system employing human gamma-globulin dot-blotted onto nitrocellulose as a model. Human gamma-globulin is dissolved in PBS pH 7.4 to give a solution of 10 mg/ml. This solution is then diluted tenfold for four further times to give solutions of 1 mg/ml, 100 µg/ml, and 1 µg/ml. 5 µl of each dilution, containing respectively 50 µg, 5 µg, 500 ng, 50 ng, 5 ng and PBS control are applied to nitrocellulose membrane (HYBOND, Amersham International) and incubated in a humid atmosphere to permit immobilisation. The membrane is then washed (three 5 minute cycles) in wash buffer PBS/0.05% TWEEN 20) and then blocked for one hour at room temperature in wash buffer. The membrane is then incubated in a solution containing goat anti-(human immunoglobulin G) conjugated to glucose oxidase in wash buffer plus bovine serum albumin 0.5% for one hour at room temperature. The membrane is then washed for three cycles of 5 minutes in wash buffer. The membrane is then blotted dry and a solution containing 1% glucose, 1 µg/ml acridinium salt in PBS pH 7.4 is applied to membrane. The presence on the membrane of the complex [human gamma-globulin/goat anti-(human immunoglobulin)-glucose oxidase] at the positions of the original dot blotting, are then visualised by placing the soaked membrane in a light tight box adjacent to the exposed emulsion of a POLAROID (TM) film; such apparatus is commercially available (for example from Amersham International). A highly sensitive POLAROID film is used in this example (612, ISO 20 000) and an exposure of 2.5 minutes, commencing 5 minutes after addition of the acridinium/glucose solution to the membrane, was found to be optimal in this instance. A sample developed image is provided in the Figure.

What is claimed is:

1. A method of determining in a medium the presence or amount of an analyte which is capable of binding to a ligand partner to form a ligand complex, which method comprises:
    (a) contacting said medium with either:
        (i) said ligand partner conjugated with an enzyme consisting of an enzyme catalysing a reaction, or one or more reactions in a cascade thereof in step (c), to produce hydrogen peroxide, or
        (ii) said ligand partner and either a competing analyte or an analog of said analyte, said competing analyte or analyte analog being capable of forming a ligand complex with said ligand partner and said competing analyte or analyte analog being conjugated with an enzyme consisting of an enzyme catalysing a reaction, or one or more reactions in a cascade thereof in step (c), to produce hydrogen peroxide,
    (b) separating complexed and uncomplexed enzyme conjugates resulting from step (a),
    (c) contacting said complexed or uncomplexed enzyme conjugate with a corresponding enzyme substrate to cause said reaction or cascade of reactions to occur to produce hydrogen peroxide;
    (d) contacting said hydrogen peroxide with a substance capable of exhibiting chemiluminescence in the presence of hydrogen peroxide selected from the group consisting of acridinium compounds and analogs thereof each having a conjugate base with a pKa less than 9 to generate a chemiluminescent reaction, and
    (e) detecting the occurrence of said chemiluminescent reaction to determine the presence or amount of said analyte.

2. The method according to claim 1, wherein said enzyme is conjugated directly to said ligand partner.

3. The method according to claim 1, wherein said enzyme is conjugated indirectly to said ligand partner.

4. The method according to claim 3, wherein said enzyme is conjugated via an intermediate ligand binding complex.

5. The method according to claim 4, wherein said enzyme is conjugated via an avidin-biotin ligand complex.

6. The method according to claim 1, wherein said enzyme is an oxidase.

7. The method according to claim 6, wherein said oxidase is glucose oxidase.

8. The method according to claim 7, wherein said step (d) occurs at a pH of from 5 to 7.

9. The method according to claim 1, wherein said enzyme is capable of generating an oxidase substrate, and said method includes catalysing said oxidase substrate with an oxidase to produce said hydrogen peroxide.

10. The method according to claim 9 wherein said enzyme is glucose synthetase.

11. The method according to claim 1, wherein said chemiluminescent substance has a conjugate base with a pKa of less than 8.

12. The method according to claim 11, wherein said chemiluminescent compound is an acridinium salt.

13. The method according to claim 12, wherein said acridinium salt is an acridinium phenyl ester.

14. The method according to claim 13, wherein the phenyl moiety of said acridinium phenyl ester includes at least one electron withdrawing group.

15. The method according to claim 14, wherein said at least one electron withdrawing group is selected from the group consisting of one or more halogen, carbonyl and nitro groups.

16. The method according to claim 12, wherein said acridinium salt is an acridinium amide, thio-ester or aliphatic ester.

17. The method according to claim 12, wherein at least one hydrophilic group is present on said acridinium salt to improve the solubility of said salt in an aqueous medium.

18. The method according to claim 1, wherein said chemiluminescent analog is selected from the group consisting of phenanthridine, quinoline and benzacridine.

19. The method according to claim 1, wherein said enzyme conjugated to said ligand partner is selected form the group consisting of glucose oxidase, xanthine oxidase, uricase and galactose oxidase.

20. The method according to claim 1, wherein said complexed and uncomplexed enzyme conjugates in step (b) are separated prior to step (c).

21. A kit for use in the assay or detection in a sample of an analyte which is capable of combining with a ligand partner to form a ligand complex, which kit comprises:
    a first reagent containing either:
        (i) a ligand partner conjugated with an enzyme, said enzyme being capable of catalysing a reaction or one or more reactions in a cascade thereof to produce hydrogen peroxide, or
        (ii) a ligand partner and either a competing analyte or an analog of said analyte capable of forming a ligand complex with said ligand partner, said competing analyte or analyte analog being conjugated with an enzyme, said enzyme being capable of catalysing a reaction, or one or more reactions in a cascade thereof, to produce hydrogen peroxide; and
    a second reagent comprising a chemiluminescent compound selected from the group consisting of acridinium compounds and analogs thereof having a conjugate base with a pKa less than 9, which react with hydrogen peroxide to yield a chemiluminescent reaction.

22. The kit according to claim 21, further including a substrate for said enzyme.

23. The kit according to claim 21, further including means for facilitating physical or chemical isolation of ligand binding complexes.

24. The kit according to claim 21, wherein said second reagent is buffered to a pH in the range of from 5 to 7.

25. The kit according to claim 21, wherein said chemiluminescent analog is selected from the group consisting of phenanthridine, quinoline and benzacridine.

26. The method according to claim 21, wherein said enzyme conjugated to said ligand partner is selected from the group consisting of glucose oxidase, xanthine oxidase, uricase and galactose oxidase.

27. A kit for use in the assay or detection in a sample of an analyte which is capable of combining with a ligand partner to form a ligand complex, in which method said sample is first contacted with either:

(i) a moiety comprising said ligand partner conjugated with an intermediate ligand partner capable of binding with a respective complementary intermediate ligand partner in and intermediate ligand binding complex, or (ii) said ligand partner and a moiety comprising competing analyte or an analog of said analyte, said competing analyte or analyte analog being capable of forming a ligand complex with said ligand partner and being conjugated with an intermediate ligand partner capable of binding with a respective complementary intermediate ligand partner in an intermediate ligand binding complex, said kit comprising a first reagent containing either:

(i) a moiety comprising said ligand partner conjugated with said intermediate ligand partner, or (ii) said ligand partner and a moiety comprising competing analyte or an analog of said analyte, said competing analyte or analyte analog being capable of forming a ligand complex with said ligand partner and being conjugated with said intermediate ligand partner, a second reagent containing a conjugate of said complementary intermediate ligand partner coupled to an enzyme, said enzyme being capable of catalysing a reaction or one or more reactions in a cascade thereof, to produce hydrogen peroxide, and a third reagent comprising a chemiluminescent compound selected from a group consisting of acridinium compounds and analogs thereof having a conjugate base with a pKa less than 9 which compound reacts with hydrogen peroxide to yield a chemiluminescent reaction.

28. The kit according to claim 27, wherein said chemiluminescent compound is selected from the group consisting of phenanthridine, quinoline and benzacridine.

* * * * *